(12) United States Patent
Schaeffer-Korbylo et al.

(10) Patent No.: US 8,906,349 B2
(45) Date of Patent: Dec. 9, 2014

(54) ORAL CARE COMPOSITION

(75) Inventors: Lyndsay Schaeffer-Korbylo, Flemington, NJ (US); Andre Michelle Morgan, Robbinsville, NJ (US); Davide Miksa, Doylestown, PA (US); Laurence Du-Thumm, Princeton, NJ (US); Michael Prencipe, Princeton Junction, NJ (US); Evangelia S. Arvanitidou, Princeton, NJ (US); Gregory Szewczyk, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/387,780

(22) PCT Filed: Aug. 12, 2009

(86) PCT No.: PCT/US2009/053500
§ 371 (c)(1),
(2), (4) Date: Jan. 30, 2012

(87) PCT Pub. No.: WO2011/019342
PCT Pub. Date: Feb. 17, 2011

(65) Prior Publication Data
US 2012/0128599 A1  May 24, 2012

(51) Int. Cl.
*A61Q 11/00* (2006.01)
*A61K 8/00* (2006.01)
*A61K 8/20* (2006.01)
*A61K 8/34* (2006.01)
*A01N 49/00* (2006.01)
*A61K 8/35* (2006.01)

(52) U.S. Cl.
CPC .......... *A61K 8/342* (2013.01); *A01N 49/00* (2013.01); *A61K 8/35* (2013.01); *A61Q 11/00* (2013.01); *A61K 8/347* (2013.01)
USPC ............. 424/49; 424/48; 424/401; 424/58; 514/729

(58) Field of Classification Search
USPC .................. 424/49, 48, 401, 58; 514/729
See application file for complete search history.

(56) References Cited

U.S. PATENT DOCUMENTS

| | | | |
|---|---|---|---|
| 4,294,894 A * | 10/1981 | Vellucci | 424/49 |
| 5,116,602 A | 5/1992 | Robinson et al. | |
| 5,256,401 A * | 10/1993 | Duckenfield et al. | 424/49 |
| 5,424,059 A * | 6/1995 | Prencipe et al. | 424/52 |
| 2004/0057908 A1 | 3/2004 | Bowen et al. | |
| 2005/0019431 A1 | 1/2005 | Modak et al. | |
| 2006/0099237 A1 | 5/2006 | Modak et al. | |

FOREIGN PATENT DOCUMENTS

| | | |
|---|---|---|
| EP | 0348560 | 1/1990 |
| EP | 2014295 * | 1/2009 |
| JP | 58213706 | 12/1983 |
| JP | S63-33326 | 2/1988 |
| JP | H01-151512 | 6/1989 |
| JP | H04-202121 | 7/1992 |
| JP | H08-151324 | 6/1996 |
| JP | 2005-015369 | 1/2005 |
| JP | 2005298357 | 10/2005 |
| JP | 2007-008843 | 1/2007 |
| JP | 2009-149535 | 7/2009 |
| RU | 2241438 | 12/2004 |
| RU | 2006135434 | 4/2008 |
| WO | WO 99/66796 | 12/1999 |
| WO | WO 00/62744 | 10/2000 |
| WO | WO 2005/009352 | 2/2005 |
| WO | WO 2007/077573 | 7/2007 |

OTHER PUBLICATIONS

Szalontai et al., 1975, "Further details on the bactericidal and fungicidal action of biologically active substances of *Matricaria chamomilla* L.", Pharmaz. Ztg. 120, 982 (Translation provided).
Szalontai et al., 1975, "Further details on the bactericidal and fungicidal action of biologically active substances of *Matricaria chamomilla* L.", Dtsch. Apoth. Ztg. 115, 912 (Translation provided).
Issac, 1980, "Chamomile Therapy—Experience and Confirmation", Dtsch. Apoth. Ztg. 120, 567-570 (Translation provided).
Luppold, 1984, "*Matricaria chamomilla*—an old and a new medicinal plant", Pharmazie in unserer Zeit 13(3), p. 65-70 (Translation provided).
Brehm-Stecher et al., 2003, "Sensitization of *Staphylococcus aureus* and *Escherichia coli* to Antibiotics by the Sesquiterpenoids Nerolidol, Farnesol, Bisabolol, and Apritone", Antimicrobial Agents and Chemotherapy 47(10), p. 3357-3360.
Aas et al., 2005, "Defining the normal bacterial flora of the oral cavity", J. Clin. Microbiology 43(11), p. 5721-32.
Data Base GNPD [Online] Mintel; "Oral Spray," XP002616749, Sep. 2006.
Data Base GNPD [Online] Mintel; "Toothpaste," XP002616750, May 2007.
Database DNPD [Online] Mintel; "Toothpaste for Sensitive Teeth," XP002616748, Nov. 2008.
Shintre et al., "Efficacy of an alcohol-based healthcare hand rub containing synergistic combination of farnesol and benzethonium chloride," International Journal of Hygiene and Environmental Health, 2006 209:477-487.
Written Opinion of the International Searching Authority in International Application No. PCT/US2009/053500 mailed Feb. 3, 2011.

* cited by examiner

*Primary Examiner* — Lezah Roberts
(74) *Attorney, Agent, or Firm* — Howard C. Lee

(57) ABSTRACT

Disclosed are oral care compositions and the use of such oral care compositions for treating conditions caused by biofilm formation. Also disclosed are methods for inhibiting biofilm formation and/or degrading biofilm. The oral care composition includes a sesquiterpenoid and an antimicrobial agent, in which the sesquiterpenoid and the antimicrobial agent are present in an amount effective to inhibit and/or degrade a biofilm in the oral cavity.

15 Claims, 6 Drawing Sheets

ORAL CARE COMPOSITION

CROSS-REFERENCE TO RELATED APPLICATIONS

This application is a national stage entry under 35 U.S.C. §371 of International Patent Application No. PCT/US2009/053500, filed Aug. 12, 2009, the contents of which are incorporated herein by reference.

The present invention relates to an oral care composition and the use of such an oral care composition for treating conditions caused by biofilm formation. The present invention also relates to a method for inhibiting biofilm formation and/or degrading biofilm.

BACKGROUND OF THE INVENTION

Bisabolol is a natural monocyclic sesquiterpene alcohol. It is commonly found in nature as the principle extract of chamomile. It is used in the cosmetics industry specifically for its skin healing properties, as well as its anti-inflammatory, anti-fungal, and anti-bacterial benefits.

Szalontai, M; Verzár-Petri, G.; Flórián, E.; Gimpel, F., Pharmaz. Ztg, 120, 982 (1975) and Szalontai, M., Verzár-Petri, G.; Flórián, E.; Gimpel, F., Dtsch. Apoth. Ztg. 115, 912 (1975) disclose the bactericidal and fungicidal action of biologically active substances of chamomile including α-bisabolol.

Issac O., Dtsch. Apoth. Ztg 120, 567-570 (1980) discloses that bisabolol has antimicrobial and antimycotic effects.

Luppold O., Pharmazie in unserer Zeit, 13,(1984), 3, p 65-70 discloses that chamomile is an effective remedy in traditional medicine. This document discloses that bisabolol, especially (−)-α-bisabolol is important for the pharmacological action of chamomile oil and have antiphlogistic, spamolytic and antibacterial activity.

Sesquiterpenoids including bisabolol have also been found to increase bacterial permeability to antimicrobial agents. Brehm-Stecher, B. F., Johnson, E. A., Antimicrobial Agents and Chemotherapy 47(10), (2003), p 3357-3360 and WO99/66796 each disclose that the sesquiterpenoids nerolidol, farnesol, bisabolol and apritone were found to enhance non-specifically the permeability of cultured bacterial cells to certain exogenous chemical compounds including antimicrobial agents.

A biofilm is a structured group of microorganisms encapsulated within a self-developed polymeric extracellular matrix. Biofilms are typically adhered to a living or inert surface. In the human or animal body biofilms can form on any internal or external surface. Biofilms have been found to be involved in a wide variety of microbial infections in the body and, therefore, cause a number of conditions including urinary tract infections, middle-ear infections, formation of dental plaque and gingivitis.

U.S. Pat. No. 5,116,602 discloses an antiplaque oral composition containing a low concentration of a sesquiterpene alcohol flavour compound to inhibit the formation of dental plaque in the presence of an additive selected from the group consisting of benzoic acid, a preservative, and a polycarboxylate and mixtures thereof, in an oral vehicle. The sesquiterpene alcohol flavour compound is not disclosed as an antimicrobial agent by itself, but must be used in combination with the additives disclosed therein.

JP 58213706 discloses a composition for the oral cavity capable of suppressing and inhibiting the formation of bacterial plaque, preventing dental caries and periodontosis, obtained by blending a composition for an oral cavity with an active ingredient selected from amygdalin, indigo, sanshool, bisabolol and rutin.

JP 2005298357 discloses a composition for the oral cavity containing a biosurfactant selected from a glycolipid produced by the microorganism, a polypeptide produced thereby and a derivative thereof and further contains one, two or more kinds of essential oil components selected from thymol, anethole, eugenol, bisabolol, farnesol and nerolidol.

Microorganisms present in a biofilm have significantly different properties from free-floating microorganisms of the same species. This is because the polymeric extracellular matrix acts to protect the microorganisms from the surrounding environment allows the microorganisms to cooperate and interact in various ways which are not exhibited by free-floating microorganisms. These complex communities of microorganisms present a unique challenge in that they are often resistant to classical means of antimicrobial control. Bacteria living in a biofilm exhibit increased resistance to antibiotics because the dense extracellular matrix and the outer layer of cells protect the interior of the biofilm from the effects of the antibiotics. Therefore, known antimicrobial agents will not have the same effect on bacteria present in a biofilm.

There is a need in the art to provide an improved oral composition capable of inhibiting biofilm formation and degrading biofilms.

BRIEF SUMMARY OF THE INVENTION

In a first aspect the present invention provides an oral care composition comprising a sesquiterpenoid and an antimicrobial agent, wherein the sesquiterpenoid and the antimicrobial agent are present in an amount effective to inhibit and/or degrade a biofilm in the oral cavity. In another aspect, the invention provides an oral care composition comprising sesquiterpenoid and an antimicrobial agent that improves the anti-biofilm (killing properties) of the antimicrobial agent.

The composition according to the present invention provides a new means for inhibiting formation of and/or degrading a biofilm in the oral cavity. The present inventors have surprisingly found that the sesquiterpenoid enhances the anti-biofilm activity of antimicrobial agents. The combination of both the sesquiterpenoid and an antimicrobial agent has been found to provide a synergistic effect on the inhibition of biofilms. In an aspect, the sesquiterpenoid is selected from the group consisting of nerolidol, farnesol, bisabolol, apritone, and mixtures thereof.

In a second aspect the present invention provides a composition as defined above for use as a medicament. The present invention also provides a composition comprising a sesquiterpenoid and an antimicrobial agent for the treatment or prevention of a condition caused by biofilm formation. The present invention also provides a method for inhibiting biofilm formation and/or degrading a biofilm in a subject comprising administering to the subject a composition comprising a sesquiterpenoid and an antimicrobial agent. The method may be used for treating or preventing a condition caused by biofilm formation.

BRIEF DESCRIPTION OF FIGURES

FIG. 4b shows an enlargement of FIG. 4a.

DETAILED DESCRIPTION OF THE INVENTION

Figure 1:
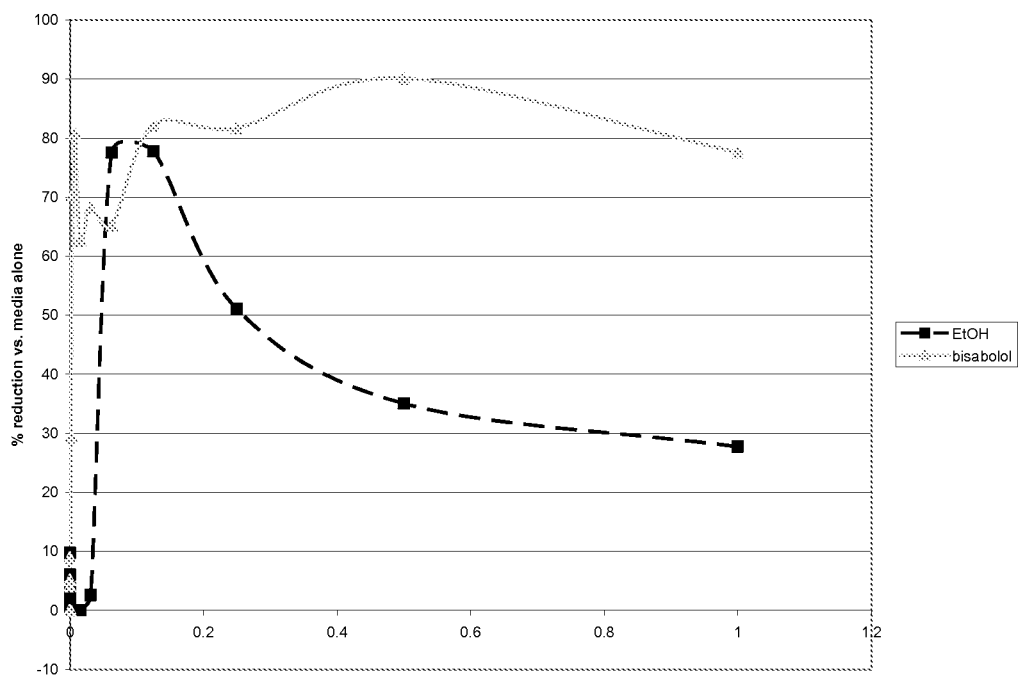
FIG. 1 shows the % reduction of biofilm formation of *A. viscosus* in the presence of serial dilutions of bisabolol or an equivalent concentration of EtOH.

It should be understood that the detailed description and specific examples, while indicating embodiments of the invention, are intended for purposes of illustration only and are not intended to limit the scope of the invention.

The following definitions and non-limiting guidelines must be considered in reviewing the description of this invention set forth herein. The headings (such as "Introduction" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

The term "biofilm" used in the context of the present invention means any group of microorganisms encapsulated within a self-developed polymeric extracellular matrix. The biofilm may be adhered to a living or inert surface. For example, in the oral cavity the biofilm may be adhered to teeth in the form of plaque. Other examples of surfaces in a subject which a biofilm may adhere to are the urinary tract, the ear, contact lenses, catheters.

The biofilm may be formed from one or more different types of microorganisms including for example bacteria, archaea, protozoa, fungi and algae. The biofilm is preferably formed from bacteria. In one embodiment the biofilm is formed from a single species of bacteria or formed from a plurality of species of bacteria. The biofilm may be formed from one or more bacteria selected from *A. viscosus*, *Lactobacillus casei*, *Streptococcus oralis*, *Fusobacterium nucleatum* and *Veillonella parvula*. Other bacteria that may form the biofilm include skin species bacteria, and one or more of the bacterial flora of the oral cavity described in Aas, J. A., et al., "Defining the normal bacterial flora of the oral cavity," *J. Clin. Microbiol.* 43(11) 5721-32 (November 2005).

Compositions

In an embodiment, the present invention provides an oral care composition comprising an anti-microbial agent and a sesquiterpenoid, wherein the sesquiterpenoid and the anti-microbial agent are present in an amount effective to inhibit and/or degrade a biofilm in the oral cavity. In an aspect, the sesquiterpenoid is selected from the group consisting of nerolidol, farnesol, bisabolol, apritone, and mixtures thereof.

In an embodiment, the present invention provides an oral care composition comprising bisabolol and an anti-microbial agent, in which the bisabolol and the anti-microbial agent are present in an amount effective to inhibit and/or degrade a biofilm in the oral cavity.

The present inventors have found that a composition comprising both bisabolol and an antimicrobial agent provide a synergistic effect on biofilm inhibition and/or biofilm degradation. It was found that a lower concentration of both bisabolol and an antimicrobial agent could be used to provide the same effect on biofilm inhibition when present together in a composition compared to when bisabolol and the antimicrobial agent were tested separately.

Without wishing to be bound by any theory of operation, it is thought that the antibiofilm activity of bisabolol is not caused by the antimicrobial activity of bisabolol. It is known in the art that bisabolol has antimicrobial properties i.e. it directly kills or inhibits the growth of microbes. The present inventors found that the antimicrobial activity of bisabolol is low, however, when compared to known antimicrobial agents such as Triclosan and cetyl pyridinium chloride. The present inventors also found that while bisabolol moderately inhibited biofilm formation alone, it had much improved activity when combined with an antimicrobial agent. Further, it was found that an antimicrobial agent had improved activity against biofilms when combined with bisabolol.

The bisabolol in the composition according to the present invention is not particularly limited and may be any naturally occurring or synthetic form of bisabolol. The bisabolol may be α-(−)-bisabolol, the enantiomer α-(+)-bisabolol or the racemic mixture α-(±)-bisabolol.

In an aspect, the sesquiterpenoid is present in the composition in an amount effective to inhibit and/or degrade a biofilm in the oral cavity. Preferably, the sesquiterpenoid is present in an amount suitable to prevent or treat a condition caused by biofilm formation, such as a condition selected from dental plaque, tooth decay, halitosis, periodontal disease or gingivitis. In another aspect, the bisabolol is present in the composition in an amount effective to inhibit and/or degrade a biofilm in the oral cavity. Preferably, the bisabolol is present in an amount suitable to prevent or treat a condition caused by biofilm formation, such as a condition selected from dental plaque, tooth decay, halitosis, periodontal disease or gingivitis.

Typically the sesquiterpenoid is present in the composition at a concentration of 0.0001 to 1% by weight, preferably from about 0.025 to 0.075%. By way of a non-limiting example, bisabolol can be present in a concentration of 0.0001 to 1% by weight, preferably from about 0.025 to 0.075%.

The antimicrobial agent in the composition according to the present invention is not particularly limited, and may be selected from halogenated diphenyl ether (triclosan), herbal extracts or essential oils (e.g., rosemary extract, thymol, menthol, eucalyptol, methyl salicylate), bisguanide antiseptics (e.g., chlorhexidine, alexidine, or octenidine), phenolic antiseptics, hexetidine, povidone iodine, delmopinol, salifluor, metal ions and their salts (e.g., zinc chloride, zinc lactate, zinc citrate, stannous fluoride, and stannous chloride), sanguinarine, propolis, oxygenating agents (e.g., hydrogen peroxide, buffered sodium peroxyborate, or peroxycarbonate), cetyl pyridinium chloride, magnolia extract, magnolol, honokiol, butyl magnolol, propyl honokiol, and mixtures thereof. Anti-attachment agents such as Solrol also can be included, as well as plaque dispersing agents such as enzymes (papain, glucoamylase, etc.).

As discussed herein, the antimicrobial agent has an improved activity of inhibiting biofilm formation and/or degrading biofilms when provided with bisabolol in the composition according to the present invention. Accordingly, a lower concentration of the antimicrobial agent is required to provide the same activity compared to a composition comprise the antimicrobial agent without bisabolol. The antimicrobial agent is present in the composition in an amount effective to inhibit and/or degrade a biofilm in the oral cavity. Preferably, the antimicrobial agent is present in an amount suitable to prevent or treat a condition caused by biofilm formation, such as a condition selected from dental plaque, tooth decay, periodontal disease, halitosis, or gingivitis.

Typically the antimicrobial agent is present in the composition at a concentration of from 0.01% to 1.5% by weight, preferably from 0.05% to 0.75% by weight. In one embodiment wherein the antimicrobial agent is Triclosan, Triclosan is preferably present in the composition at a concentration of 0.05% to 0.75% by weight.

In an embodiment, as set forth in detail elsewhere herein, the combination of both a sesquiterpenoid, preferably bisabolol, and an antimicrobial agent provides a synergistic effect on the inhibition of biofilm formation and/or biofilm degradation. The present inventors found a surprising reduction in Biofilm Eradication Concentration ($BEC_{50}$), which is the lowest concentration at which greater than 50% reduction in biomass is observed relative to control. The $BEC_{50}$ of bisabolol and antimicrobial agents is lower when they are tested together for biofilm inhibition compared to when they are tested separately.

Accordingly, in a preferred embodiment the bisabolol has a $BEC_{50}$ in the presence of the antimicrobial agent of 50% or less, more preferably 30% or less, most preferably 25% or less, compared to the $BEC_{50}$ of bisabolol not in the presence of the antimicrobial agent. The bisabolol preferably has a $BEC_{50}$ in the presence of the antimicrobial agent of 10 ppm to 40 ppm, more preferably 20 ppm to 30 ppm, more preferably 25 ppm to 30 ppm and most preferably 27 ppm to 28 ppm.

In a preferred embodiment the antimicrobial agent has a $BEC_{50}$ in the presence of bisabolol of 75% or less, more preferably 50% or less, most preferably 25% or less, compared to the $BEC_{50}$ of the antimicrobial agent not in the presence of bisabolol. The $BEC_{50}$ of the antimicrobial agent in the presence of bisabolol depends upon the specific antimicrobial agent used in the composition. The antimicrobial agent may typically have a $BEC_{50}$ of 700 ppm or less in the presence of bisabolol. The antimicrobial agent preferably has a $BEC_{50}$ of 20 ppm or less, more preferably 6 ppm or less, most preferably 2 ppm or less in the presence of bisabolol. In one embodiment, wherein the antimicrobial agent is Triclosan, Triclosan has a $BEC_{50}$ of from 1 ppm to 3 ppm in the presence of bisabolol, more preferably a $BEC_{50}$ of 1.5 ppm to 2 ppm.

In an embodiment, the pH of the oral compositions containing the sesquiterpenoid and an antimicrobial agent can range from 3 to 9, preferably, from 4 to 8, and most preferably the pH is about 5. The oral compositions also preferably include a buffer selected from sodium phosphate, tetrasodium pyrophosphate, tetra potassium pyrophosphate, sodium citrate, and mixtures thereof.

The composition according to the present invention may also comprise one or more further agents typically selected from an anti-plaque agent, a whitening agent, antibacterial agent, cleaning agent, a flavouring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agent, nutrient and combinations thereof. Various components that may be added to the composition include, for example, a sweetening agent such as saccharin, or sodium saccharin, alcohols such as ethanol, fluoride ion sources such as sodium fluoride, as well as glycerine, sorbitol, propylene glycol, polyethylene glycols, Poloxomer polymers such as POLOXOMER 407, PLURONIC F108, (both available from BASF Corporation), alkyl polyglycoside (APG), polysorbate, PEG40, castor oil, menthol, and the like.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof One or more colorants are optionally present in a total amount of about 0.001% to about 20%, for example about 0.01% to about 10% or about 0.1% to about 5%.

The compositions of the present invention further comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-l-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The compositions of the present invention optionally comprise a fluoride ion source and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof One or more fluoride ion sources are optionally present in an amount providing a clinically efficacious amount of soluble fluoride ion to the oral composition.

The compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof One or more saliva stimulating agents are optionally present in saliva stimulating effective total amount.

The compositions of the present invention optionally comprise a nutrient. Suitable nutrients include vitamins, minerals, amino acids, and mixtures thereof Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In various embodiments, the oral composition according to the present invention is not intentionally swallowed, but is rather retained in the oral cavity for a time sufficient to effect the intended utility. In other portable embodiments (such as a lozenge, mint, bead, wafer, liquid formulated for oral application from a small portable nebulizer, liquid formulated for oral application from a small portable drop-generating bottle, or a soft pliable tablet), the oral composition is intentionally swallowed, optionally after retention in the oral cavity for a time sufficient to effect intended utility.

The composition according to the present invention preferably comprises an orally acceptable carrier in a product such as mouthwash, toothpaste, dental cream, chewing gum, denture adhesive or portable dosage article such as, without limitation, a lozenge, a mint, bead, wafer, liquid formulated for oral application in a small portable nebulizer (spray bottle), liquid formulated for oral application in a small portable drop-generating bottle, or a soft pliable tablet ("chewie"). As used herein, an "orally acceptable carrier" refers to a material or combination of materials that are safe for use in the compositions of the present invention, commensurate with a reasonable benefit/risk ratio.

The present invention also provides portable dose article comprising an oral care composition as defined above, wherein the portable dose article is selected from a lozenge, a mint, a bead, a wafer, a small portable nebulizer containing said admixture in liquid formulated for oral application as a spray, a small portable bottle containing said admixture in liquid formulated for oral application as a drop, and a soft pliable tablet.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

Methods of Use

The composition according to the present invention may be administered to or applied to a human or other animal subject. The composition may be suitable for administration or application to the oral cavity of a human or animal subject for inhibiting biofilm formation and/or biofilm degradation.

Accordingly, the present invention provides a composition as defined above for use as a medicament.

The present invention also provides a composition comprising a sesquiterpenoid (e.g., bisabolol) and an antimicrobial agent for the treatment or prevention of a condition caused by biofilm formation. The present invention also provides the use of a composition comprising a sesquiterpenoid and an antimicrobial agent for the manufacture of a medicament for the treatment or prevention of a condition caused by biofilm formation. In an embodiment, the condition prevented or treated is selected from dental plaque, tooth decay, periodontal disease, halitosis, and gingivitis. Preferably the composition is an oral care composition as defined above.

The present invention also provides a method for inhibiting biofilm formation and/or degrading a biofilm in a subject comprising administering to the subject a composition comprising sesquiterpenoid, preferably bisabolol, and an antimicrobial agent. The method also is capable of enhancing antimicrobial activity of an antimicrobial agent by combining the antimicrobial agent with a sesquiterpenoid, preferably bisabolol, in a composition for oral as well as non-oral applications (e.g., skin, hair, nails, etc.). In an embodiment, the composition is an oral composition as defined above and the composition is applied to an oral cavity. In a preferred embodiment the method is for treating or preventing a condition caused by biofilm formation. Preferably, the condition caused by biofilm formation is a condition of the oral cavity and may be selected from dental plaque, tooth decay, periodontal disease, halitosis, or gingivitis.

A composition comprising a sesquiterpenoid (e.g., bisabolol) and an antimicrobial agent is capable of significantly inhibiting biofilm formation and/or degrading an existing biofilm in a subject. The composition is particularly useful for inhibiting biofilm formation and/or degrading a biofilm in the oral cavity. A medicament comprising the composition according to the present invention may be administered to a patient. The medicament may be administered less frequently and/or at lower concentrations compared to known antibacterial oral compositions due to the presence of both bisabolol and an antimicrobial agent which provides a synergistic anti-biofilm effect.

The present invention also provides the use of bisabolol for enhancing the anti-biofilm activity of an antimicrobial agent. The bisabolol and antimicrobial agent are preferably as described herein.

Each and every reference cited herein is hereby incorporated by reference in its entirety. Various embodiments now will be described with reference to the following non-limiting examples

EXAMPLES

Example 1

Minimum Inhibitory Concentration of Bisabolol

The inhibitory effect of bisabolol, Triclosan and cetyl pyridinium chloride (CPC) was tested against *A. viscosus*, a common oral bacteria.

The minimum inhibitory concentration for actives was determined by incubating *Actinomyces viscosus* bacteria with serial dilutions of the active for 24 hours and determining the lowest concentration at which growth of this species was inhibited. Briefly, 100 µl final volume actives were serially diluted in 0.5× tryptic soy broth (TSB) across duplicate wells of a 96-well flat bottom microtiter plate. An overnight culture of bacteria was diluted to an $OD_{610}$ ~0.2 and 100 µl of this was added to each well. Plates were incubated overnight at 37° C. $OD_{610}$ was read for each well and the MIC was determined as the concentration of active in the last well where bacterial growth was inhibited. The Minimum Inhibitory Concentration (MIC) is provided in Table 1 below.

TABLE 1

Minimum inhibitory concentration of two known antibacterial agents and bisabolol against a common oral bacterium (*A. viscosus*).

| Compound | MIC (*A. viscosus*) |
|---|---|
| Bisabolol | 125 ppm |
| Triclosan | 3.5 ppm |
| CPC | <1 ppm |

It can be seen from Table 1 that bisabolol has a relatively high MIC when compared to Triclosan and CPC. This suggests that bisabolol does not act as an antibacterial agent. Accordingly, the bioenhancing and biofilm inhibition effects of bisabolol, as demonstrated in Examples 2 to 6 are not believed to be due to its antimicrobial properties.

Example 2

Bisabolol Inhibition of Biofilm Formation

The effect of different concentrations of bisabolol on the inhibition of *A. viscosus* biofilm formation was tested.

*A. viscosus* bacteria were grown for 24 hours in the presence of serial dilutions of bisabolol or an equivalent concentration of EtOH. Wells were stained to visualize biofilm formation. The results are shown in FIG. 1 where the x-axis represents the concentration of bisabolol (or an equivalent solution of EtOH in media) and the y-axis represents the percent reduction in biofilm relative to control wells grown in media alone.

The results show that bisabolol alone was able to inhibit the formation of single-species biofilms at a concentration as low as 110 ppm.

Example 3

Bisabolol and Triclosan Inhibition of Biofilm Formation

A composition comprising bisabolol, a composition comprising the antibacterial agent Triclosan and a composition comprising both bisabolol and Triclosan were tested for anti-biofilm activity.

A composition comprising bisabolol (0.7%), a composition comprising Triclosan (0.05%) and a composition comprising bisabolol (0.7%) and Triclosan (0.05%) were each serially diluted in a 96-well plate. *A. viscosus* cultures were added to each well and plates were incubated at 37° C. to allow biofilm formation to occur. Following biofilm formation, supernatants were removed and wells were stained with 0.6% crystal violet for 15 min. Biofilm biomass was quantified by reading the absorbance of each well at 590 nm and the percentage reduction in biomass relative to a control of media alone was calculated.

Results are reported as the Biofilm Eradication Concentration ($BEC_{50}$), which is the lowest concentration at which greater than 50% reduction in biomass is observed relative to control.

Figure 2:
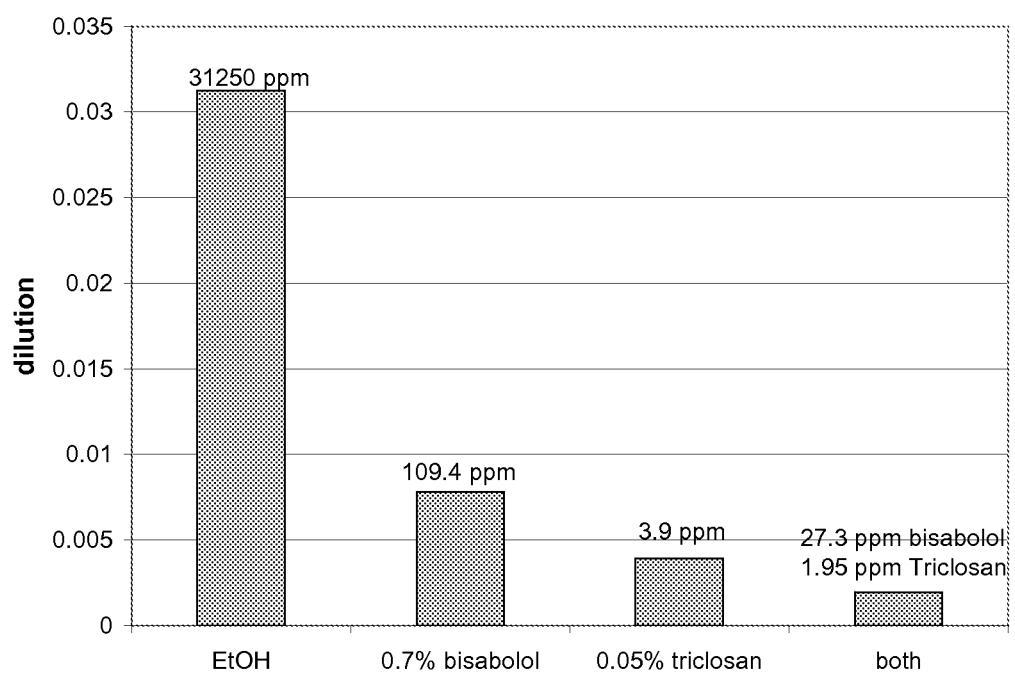
FIG. 2 shows the Biofilm Eradication Concentration$_{50}$ (BEC$_{50}$) for bisabolol and Triclosan alone or in combination.

FIG. 2 shows the $BEC_{50}$ for bisabolol and Triclosan alone or in combination with one another. $BEC_{50}$ is defined as the minimum concentration at which a greater than 50% reduction of biofilm formation is observed.

Consistent with the results in FIG. 1, bisabolol alone inhibited biofilm formation at concentrations as low as 110 ppm. Triclosan alone inhibited biofilm formation at concentrations of approximately 3.9 ppm, consistent with other studies of this organism. However, when the two actives were combined, biofilm inhibition was observed at 27.3 ppm of bisabolol and 1.95 ppm of Triclosan, suggesting enhancement of activity and a synergistic effect on biofilm inhibition. In other words, the amounts of bisabolol and Triclosan required to achieve effective biofilm formation was reduced by more than 50% and up to 75-80% when the two actives were combined.

Example 4

Bisabolol Enhancement of Antibiofilm Activity of Triclosan

The antibiofilm effect of a composition comprising Triclosan alone and a composition comprising both bisabolol and Triclosan was determined To determine bioenhancement activity, 50 µl serial dilutions of test actives were made in quadruplicate rows of a 96 well flat bottom microtiter plate in 0.5× TSB. A total volume of 50 µl bisabolol was added to two of the rows containing the test active and two rows of pure media to twice the final concentration indicated. An overnight culture of *A. viscosus* bacteria was diluted to an $OD_{610}$~0.4 in 0.5× TSB and 100 µl added to each well of the 96-well plate, bringing the final volume to 200. Plates were incubated for 24 h at 37° C. to allow for bacterial growth and biofilm formation. Supernatants were decanted from the plates and 50 µl of 0.03% Gram's crystal violet was added to each well. Plates were allowed to stain for 15 min before the dye was decanted off. Each well was washed one time with a 10 mM tris, 1 mM EDTA wash buffer. Plates were allowed to dry and stained plates were read on a Perkin Elmer EnVision microplate reader for absorbance at 590 nm. Absorbances were compared to the absorbance of wells treated with media alone or the bisabolol alone, as appropriate. Results were reported as the lowest concentration at which a >50% reduction in biofilm relative to control is observed.

Figure 3:
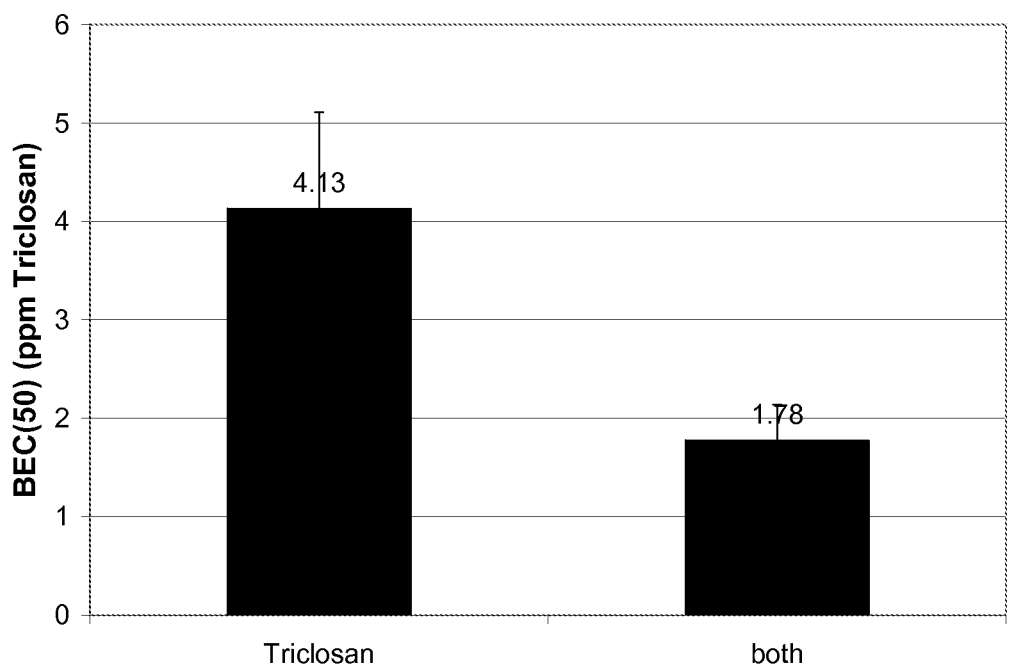
FIG. 3 shows the $BEC_{50}$ of Triclosan and effect of the addition of 5 ppm bisabolol on the $BEC_{50}$ of Triclosan.

This study was repeated with a variety of bisabolol concentrations ranging from 5-1000 ppm. Representative data from experiments performed at 5 ppm of bisabolol are shown in FIG. 3, where the Triclosan in the composition comprising Triclosan alone had a $BEC_{50}$ of 4.13ppm whereas the Triclosan in the composition comprising bisabolol had a $BEC_{50}$ of 1.78. Again, it can be seen that when bisabolol is combined with an anti-microbial agent, the amount of anti-microbial agent needed to achieve the same or similar biofilm reduction was reduced by well over 50% and up to 75%.

In view of these results it is clear that even at the low concentration of 5 ppm bisabolol, the formation of single-species biofilm was inhibited at concentrations of Triclosan as low as 1.78 ppm, compared to 4.13 ppm of Triclosan alone. This indicates that, for a single-species, static biofilm model, bisabolol is able to increase the efficacy of Triclosan, and thereby lower the minimum concentration required for biofilm inhibition.

Example 5

Bisabolol Enhancement of Antibiofilm Activity of Antimicrobial Agents

The effect of bisabolol on the antibiofilm activity of 12 different antimicrobial agents was tested.

These studies were completed in the presence or absence of 50 ppm of bisabolol and $BEC_{50}$ values were again compared for a panel of known antimicrobial agents of varying degrees of efficacy. The results are shown in FIGS. 4a and 4b.

Figure 4A:
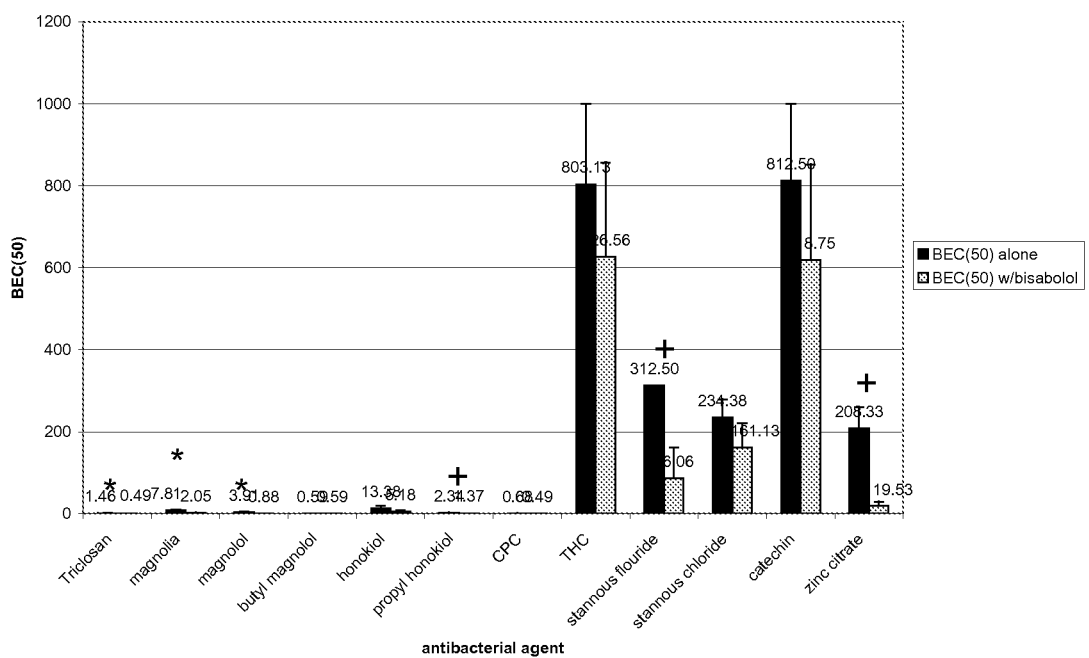
FIG. 4a shows the $BEC_{50}$ of 12 known antimicrobial agents in the absence (black bars) and presence (gray bars) of 50 ppm bisabolol.
Figure 4B:
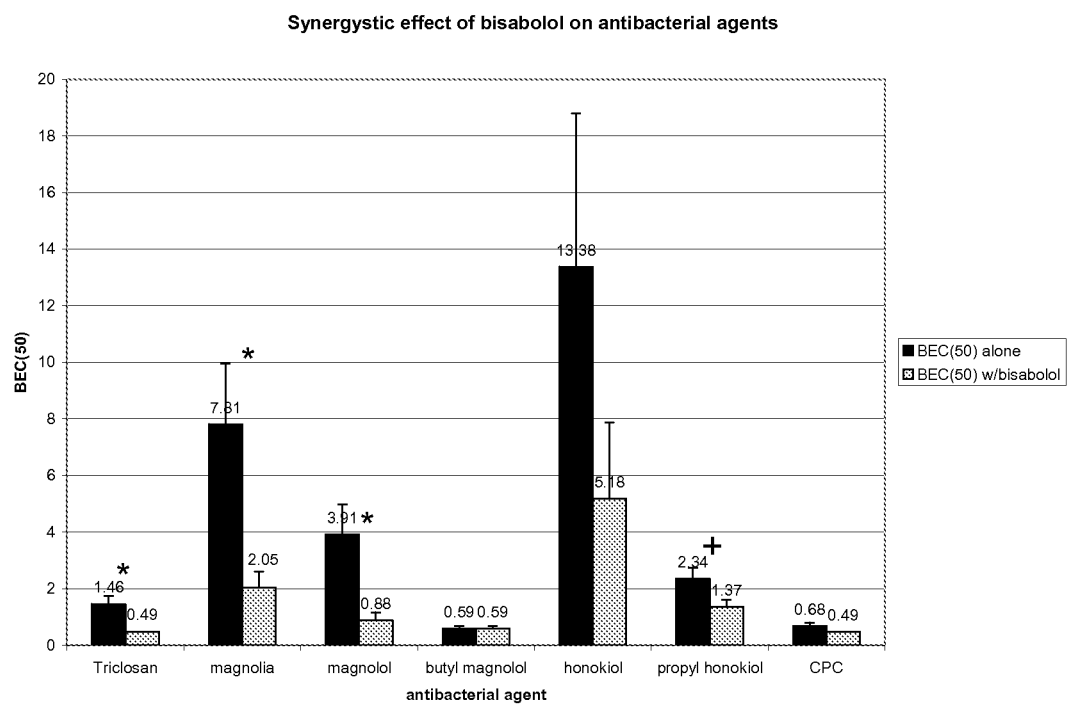

FIG. 4a shows the $BEC_{50}$ of 12 known antimicrobial agents in the absence (black bars) and presence (gray bars) of 50 ppm bisabolol. The data described in Table 2 (below) is the raw data used to generate the graph depicted in FIG. 4a.

TABLE 2

| Active Ingredient | BEC(50) alone | BEC(50) w/bisabolol |
| --- | --- | --- |
| Triclosan | 1.46484375 | 0.48828125 |
| magnolia | 7.8125 | 2.05078125 |
| magnolol | 3.90625 | 0.87890625 |
| butyl magnolol | 0.5859375 | 0.5859375 |
| honokiol | 13.37890625 | 5.17578125 |
| propyl honokiol | 2.34375 | 1.3671875 |
| CPC | 0.68359429 | 0.48828197 |
| THC | 803.125 | 626.5625 |
| stannous flouride | 312.5 | 86.05957031 |
| stannous chloride | 234.375 | 161.1328125 |
| catechin | 812.5 | 618.75 |
| zinc citrate | 208.3333333 | 19.53125 |

FIG. 4b shows an enlarged area of FIG. 4a. * indicates significant difference (p<0.05); + indicates a trend towards significance (p<0.1). The data described in Table 3 (below) is the raw data used to generate the graph depicted in FIG. 4b.

TABLE 3

| Active Ingredient | BEC(50) alone | BEC(50) w/bisabolol |
| --- | --- | --- |
| Triclosan | 0.281909311 | 0 |
| magnolia | 2.13954124 | 0.543726989 |
| magnolol | 1.06977062 | 0.284714448 |
| butyl magnolol | 0.09765625 | 0.09765625 |
| honokiol | 5.410015228 | 2.690425257 |
| propyl honokiol | 0.390625 | 0.239207983 |
| CPC | 0.119603771 | 1.7999E-07 |
| THC | 196.875 | 229.4322561 |
| stannous flouride | 0 | 75.5612605 |
| stannous chloride | 45.10548978 | 59.86840546 |
| catechin | 187.5 | 233.5192712 |
| zinc citrate | 52.08333333 | 9.765625 |

These results show that the ability of bisabolol to enhance the activity of antimicrobial agents is non-specific.

Example 6

Bisabolol and Antimicrobial Agent Inhibition of Multispecies Biofilms

The ability of compositions comprising Triclosan and bisabolol either alone or in combination to inhibit biofilm formation were tested in a multispecies model where the biofilms comprised five representative oral bacterial species: *A. viscosus, Lactobacillus casei, Streptococcus oralis, Fusobacterium nucleatum* and *Veillonella parvula*. Saliva coated hydroxyapatite (HAP) disks were inoculated with this five-species mix of bacteria in the presence Triclosan alone, bisabolol alone or with a 2:1 concentration of bisabolol:Triclosan. Disks were incubated for 48 h to allow biofilm formation to occur. Biofilm containing disks are were incubated in 1 ml of 0.25% trypsin solution for 45 min at 37° C. to release the biofilm and biomass was read as the $OD_{610}$ of the trypsin solution.

Figure 5:
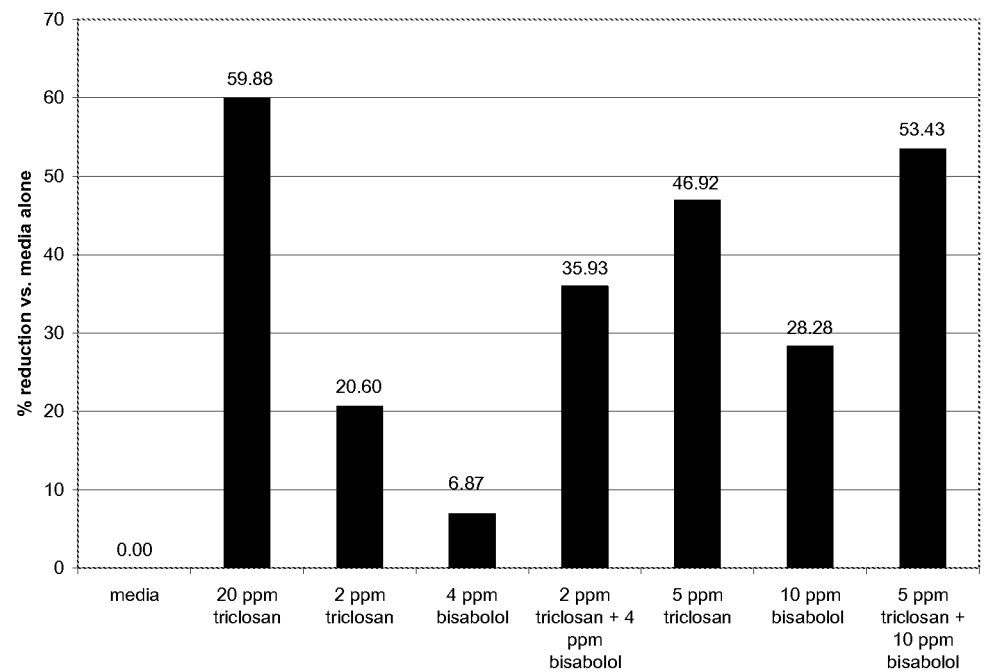
FIG. 5 shows the effect of Triclosan and bisabolol alone or in combination with 2:1 bisabolol:Triclosan on the formation of five-species biofilms.

FIG. 5 shows the results of these experiments. It can be seen that the composition comprising 20 ppm of Triclosan alone is highly effective (>60% reduction in biofilm formation), and showing additional efficacy beyond this is difficult. In order to determine any antibiofilm effect beyond that of Triclosan, it was necessary to reduce the concentration of Triclosan below the inhibitory concentration. Therefore, these experiments were conducted at 2 ppm or 5 ppm of Triclosan. FIG. 5 shows the effect of this level of Triclosan alone or in combination with a 2:1 concentration of bisabolol:Triclosan.

At these low concentrations of Triclosan, the combination of bisabolol and Triclosan was found to be more effective at inhibiting model oral biofilm formation than either bisabolol or Triclosan alone. The significant reduction of biofilm formation in the compositions comprising both bisabolol and Triclosan shows that the presence of bisabolol significantly enhances the antibiofilm efficacy of Triclosan. Since bisabolol has been shown in Example 5 to act as a nonspecific enhancer of antimicrobial activity, this same trend will likely hold for the other actives shown to be enhanced in FIG. 4a.

Example 7

Oral Composition

Table 3 (below) illustrates examples of dentifrice compositions formulated with bisabolol alone and in combination with other known oral care active ingredients. Examples of oral care approved therapeutic agents for which bisabolol has a bioenhancing effect include, but are not limited to, Triclosan, CPC, magnolia extract (natural or synthetic), magnolol, honokiol, butyl magnolol, propyl honokiol, zinc chloride, zinc lacate, zinc citrate, stannous fluoride, or stannous chloride.

TABLE 3

| Component | A % w/w | B % w/w | C % w/w | D % w/w | E % w/w | F % w/w |
|---|---|---|---|---|---|---|
| Sorbitol-Non-Browning/Non-Crystillizing | 23.94 | 19.45 | 29.8 | 19.45 | | 23.21 |
| 99.0%-101.0% Vegetable Glycerin-USP and EP | 15 | 20.00 | 20.21 | 20.00 | 40.706 | 11.5 |
| Gantrez S-97 (B.F.)-Liquid | 15 | | | | | 11.54 |
| Zeo Silica, Cationic Compatible-DP-002 | | | 15 | | | |
| Zeo 114-Synth. Amorphous PPT Silica | | | | | 12.0 | 10.0 |
| Dental Type Silica-Zeodent 105-High Cleaning Silica | 10 | 10 | | 10 | 12.0 | 10.0 |
| Dental Type Silica (Zeodent 115) Abrasive | 8.8 | 8.5 | | 8.5 | | |
| Poly(vinylpyrrolidone) (Polyclar 10) | | | 4.0 | | 1.0 | |
| Polyethylene Glycol 600 (PEG-12) | | | | | 7.0 | 3.0 |
| Trisodium Citrate Dihydrate | | | | 3.0 | | |
| Dental Type Silica-Zeodent 165-Synth. Amorphous Ppt Silica | 2.7 | 3.0 | | 3.0 | | 1.75 |
| Polysorbate 20-USP or EP | | | 2.0 | | | |
| Hydroxyethyl Cellulose 250M | | | 2.0 | | | |
| Poloxomer 407 NF | | | 1.0 | | | |
| Cocamidopropyl Betaine | | | 1.0 | | | |
| Zinc Lactate Dihydrate or Zinc Citrate Trihydrate | | | 2.0 | | 2.0 | 2.0 |
| Sodium Tripolyphosphate | | | | | 3.0 | |
| Tetrasodium Pyrophosphate | | | | | 2.0 | 2.44 |
| Sodium Lauryl Sulfate Powder-NF | 1.7 | 1.5 | | 1.5 | 1.5 | 1.5 |
| Sodium Hydroxide-50% Solution (Reagent Grade) | 1.2 | | | | | 1.25 |
| Sodium CMC-12 Type USP | 1.1 | 1.1 | | 1.1 | | 0.6 |
| Flavor | 1.0 | 1.0 | 1.4 | 1.0 | 1.3 | 1.2 |
| Citric Acid-Anhydrous | | | | | 0.6 | |
| Titanium Dioxide-USP | 0.75 | 0.5 | 0.5 | 0.5 | 0.5 | 1.0 |
| ±α-Bisabolol (Synthetic) | 0.3-1% | 0.3-1% | 0.3-1.0 | 0.3-1% | 0.3-1% | |
| Sodium Monofluorophosphate-USP | | | 0.76 | | | 0.76 |
| Cetylpyridinium Chloride | | | 0.30.75% | | | |
| *Magnolia* Extract, Magnolol, Honokiol, Butyl Magnolol, or Propyl Honokiol | | | 0.5 | | | |
| Stannous Fluoride | | | | | 0.454 | |
| Propylene Glycol-USP | 0.5 | 1.0 | | 1.0 | | |
| Iota Carrageenan (LB 9505) | 0.48 | 0.4 | | 0.4 | | |
| Carrageenan Concentrate (PS-223) | | | | | | 0.4 |
| Xanthan gum-NF | | | | | 0.3 | |
| Triclosan-USP | | | 0.3 | | | |

TABLE 3-continued

| Component | A % w/w | B % w/w | C % w/w | D % w/w | E % w/w | F % w/w |
|---|---|---|---|---|---|---|
| Sodium Saccharin USP | 0.3 | 0.3 | 0.50 | 0.3 | 0.5 | 0.3 |
| Sodium Fluoride USP | 0.243 | 0.243 | | 0.243 | | |
| Sucralose | | | 0.15 | | | |
| Demineralized Water | qs | qs | Qs | qs | qs | qs |

The invention claimed is:

1. An oral care composition comprising a sesquiterpenoid and an antimicrobial agent, wherein the sesquiterpenoid and the antimicrobial agent are present in an amount effective to inhibit and/or degrade a biofilm in the oral cavity, wherein the sesquiterpenoid is bisabolol; and
the antimicrobial agent is triclosan;
wherein the bisabolol is present in the composition at a concentration of 0.025 to 0.075% w/w; and
wherein the sesquiterpenoid has a $BEC_{50}$ in the presence of the antimicrobial agent of 25% or less compared to the $BEC_{50}$ of the sesquiterpenoid in the absence of the antimicrobial agent.

2. The oral care composition according to claim 1 wherein the sesquiterpenoid is present in the composition at a concentration of up to 1% w/w.

3. An oral care composition according to claim 1, wherein the bisabolol has a $BEC_{50}$ of 20 ppm to 30 ppm.

4. An oral care composition according to claim 1, wherein the antimicrobial agent has a $BEC_{50}$ in the presence of the sesquiterpenoid of 75% or less compared to the $BEC_{50}$ of the antimicrobial agent not in the presence of the sesquiterpenoid.

5. An oral care composition according to claim 4, wherein the antimicrobial agent has a $BEC_{50}$ in the presence of the sesquiterpenoid of 50% or less compared to the $BEC_{50}$ of the antimicrobial agent not in the presence of the sesquiterpenoid.

6. An oral care composition according to claim 3, wherein the Triclosan has a $BEC_{50}$ of from 1 ppm to 3 ppm.

7. An oral care composition according to claim 1, wherein the composition further comprises one or more agents selected from the group consisting of an anti-plaque agent, a whitening agent, a sweetening agent, a cleaning agent and a flavouring agent.

8. An oral care composition according to claim 1, wherein the composition comprises an orally acceptable carrier for a toothpaste, a dental cream, a mouthwash, a chewing gum or a denture adhesive.

9. A method of inhibiting biofilm formation and/or degrading a biofilm in a subject comprising administering to the subject the composition of claim 1.

10. The method according to claim 9, wherein the composition is applied to an oral cavity.

11. The method according to claim 10, wherein the method prevents or treats a condition caused by biofilm formation in the oral cavity.

12. The method according to claim 11, wherein the condition is selected from the group consisting of dental plaque, tooth decay, periodontal disease, halitosis, and gingivitis.

13. The method according to claim 9, wherein the biofilm is formed from a single species of bacteria.

14. The method according to claim 9, wherein the biofilm is formed from a plurality of species of bacteria.

15. The method according to claim 9, wherein the biofilm is formed from one or more bacteria selected from the group consisting of *A. viscosus, Lactobacillus casei, Streptococcus oxalis, Fusobacterium nucleatum* and *Veillonella parvula*.

* * * * *